United States Patent
Chiou et al.

(10) Patent No.: US 9,949,903 B2
(45) Date of Patent: Apr. 24, 2018

(54) WATER-IN-OIL COSMETIC COMPOSITION HAVING HIGH LEVELS OF ACTIVE INGREDIENTS

(71) Applicant: L'OREAL, Paris (FR)

(72) Inventors: Catherine Chiou, Saddle Brook, NJ (US); Carlos Crissien, Clifton, NJ (US); Raul M. Diaz, North Bergen, NJ (US); Angelike A. Galdi, Westfield, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 14/614,092

(22) Filed: Feb. 4, 2015

(65) Prior Publication Data
US 2016/0220455 A1 Aug. 4, 2016

(51) Int. Cl.
| | |
|---|---|
| *A61K 8/06* | (2006.01) |
| *A61K 8/60* | (2006.01) |
| *A61K 8/891* | (2006.01) |
| *A61Q 19/08* | (2006.01) |
| *A61K 8/37* | (2006.01) |
| *A61K 8/894* | (2006.01) |
| *A61K 8/92* | (2006.01) |

(52) U.S. Cl.
CPC .......... *A61K 8/064* (2013.01); *A61K 8/37* (2013.01); *A61K 8/602* (2013.01); *A61K 8/891* (2013.01); *A61K 8/894* (2013.01); *A61K 8/922* (2013.01); *A61Q 19/08* (2013.01)

(58) Field of Classification Search
None
See application file for complete search history.

(56) References Cited

U.S. PATENT DOCUMENTS

| | | |
|---|---|---|
| 4,767,750 A | 8/1988 | Jacquet et al. |
| 5,262,407 A | 11/1993 | Leveque et al. |
| 5,558,871 A | 9/1996 | Griat et al. |
| 5,580,549 A | 12/1996 | Fukuda et al. |
| 5,667,789 A | 9/1997 | Collin et al. |
| 6,159,479 A | 12/2000 | Pinzon |
| 2004/0208904 A1* | 10/2004 | Touitou .......... A61K 8/922 424/401 |
| 2006/0177405 A1* | 8/2006 | Morrissey .......... A61K 8/345 424/70.21 |
| 2007/0207103 A1* | 9/2007 | Masuda .......... A61K 8/345 424/64 |
| 2008/0153839 A1* | 6/2008 | Cotton .......... A61K 8/368 514/252.12 |
| 2008/0254150 A1* | 10/2008 | Rheins .......... A61K 8/042 424/725 |
| 2011/0098229 A1* | 4/2011 | Paul .......... A61K 9/0014 514/18.6 |
| 2013/0345317 A1* | 12/2013 | Chiou .......... A61Q 19/00 514/770 |

FOREIGN PATENT DOCUMENTS

| | | |
|---|---|---|
| EP | 0378936 A2 | 7/1990 |
| EP | 0570230 A1 | 11/1993 |
| FR | 2581542 A1 | 11/1986 |
| FR | 2894468 A1 | 6/2007 |
| FR | 2911496 A1 | 7/2008 |
| WO | 2051828 A2 | 7/2002 |

OTHER PUBLICATIONS

Cirebelle, "Information Bulletin," Apr. 2005, pp. 1-17.*

* cited by examiner

*Primary Examiner* — Brian Gulledge
(74) *Attorney, Agent, or Firm* — McNees Wallace & Nurick, LLC

(57) ABSTRACT

A composition for imparting anti-aging benefits onto skin containing: (a) an aqueous phase containing: (i) from about 0.5% to 10% by weight, of at least one water-soluble active ingredient; and (ii) water; and (b) an oil phase containing: (iii) at least one emulsifying crosslinked siloxane elastomer; (iv) from about 0.1% to 1% by weight, of at least one oil-soluble active ingredient; (v) wax; and (vi) oil; all weights based on the total weight of the composition.

25 Claims, No Drawings

WATER-IN-OIL COSMETIC COMPOSITION HAVING HIGH LEVELS OF ACTIVE INGREDIENTS

FIELD OF THE INVENTION

The present invention is directed to cosmetic compositions and methods of using and producing same. More specifically, the present invention is directed to a cosmetic composition in the form of a water-in-oil emulsion having an oil phase comprising an emulsifying crosslinked siloxane elastomer, at least one wax having a melting point greater than about 50° C., at least one oil-soluble anti-aging active ingredient, and, optionally, a branched- and/or linear-type silicone emulsifier and an aqueous phase comprising at least one water-soluble anti-aging active ingredient. The cosmetic composition contains one or more active ingredients which are typically difficult to formulate into water-in-oil emulsions at highly effective concentrations. The cosmetic compositions also possess a pleasing texture/sensorial experience.

BACKGROUND OF THE INVENTION

Conventional cosmetic compositions are usually in the form of emulsions either of the water-in-oil (W/O) or oil-in-water (O/W) types. O/W emulsions are usually preferred in the cosmetics field, because O/W emulsions typically have a fresher, less greasy, less tacky, and lighter feel than W/O emulsions. As W/O emulsions are close to the skin's hydrolipid film, they are more effective from a dermatological viewpoint by promoting long lasting moisturizing efficacy by providing an occlusive film and reinforcing the active ingredients into the stratum corneum. Unfortunately, their tackiness, greasiness and poor spreadability render them less appealing to consumers.

There is growing consumer demand for cosmetic products which provide anti-aging skin care benefits such as diminishing the appearance of and/or preventing wrinkles, fine lines, skin laxity, and discolorations or improving skin radiance. Unfortunately, many of the active ingredients which are used in these products are difficult to formulate into stable cosmetic compositions, especially at concentrations required for efficacy. Moreover, even when these ingredients are formulated into stable cosmetic compositions, these compositions may not appeal to the consumer because of tackiness, greasiness, and poor spreadability.

Capryloyl salicylic acid is an amphoteric active ingredient used in cosmetic compositions for anti-aging. Unfortunately, its amphoteric nature results in the destabilization of W/O emulsions making it difficult to prepare stable W/O emulsions which contain high levels of capryloyl salicylic acid.

Another anti-aging active ingredient used in cosmetic compositions is hydroxypropyl tetrahydropyrantriol. Unfortunately, due to its high electrolyte content, it too presents a formulation challenge, particularly in direct O/W emulsions, by requiring high concentrations of water phase thickeners in order to achieve a stable viscosity.

The use of high levels of these types of active ingredients presents severe stability challenges when formulating cosmetic compositions, especially W/O emulsions.

FR 2 911 496 B1 describes a W/O emulsion comprising 0.3% capryloyl salicylic acid and a wax. The emulsions obtained, however, are in the form of a hard solid having a penetration force of greater than or equal to about 40 grams. It may be postulated that the stability of this emulsion is attributed to its solid state in which the capryloyl salicylic acid is suspended in the wax matrix. These types of hard solid emulsions suffer from undesirable attributes such as poor glide and a waxy texture.

It is therefore an objective of the present invention to provide W/O emulsions which are fluid in nature, include amounts of anti-aging ingredients that were not previously possible due to stability concerns, and possess a pleasant sensorial experience when used by consumers.

BRIEF SUMMARY OF THE INVENTION

Applicants have surprisingly discovered that the use of an emulsifying crosslinked siloxane elastomer enables the formulation of a stable W/O emulsion having quantities of anti-aging active ingredients that have conventionally been known to de-stabilize W/O emulsions due to their amphoteric and high electrolyte-possessing nature. Moreover, the resultant formulations impart a velvety soft, melting and caring sensation upon application onto an end-user's skin. Without intending to be bound by theory, it is believed that the stability and texture of applicants' W/O emulsion arises from the 3-dimensional network structure of the emulsifying crosslinked siloxane elastomer which entraps the anti-aging active ingredients at the interphase of the oil and water phases, thereby allowing them to stably co-exist between the two phases. The 3-dimensional network structure improves stability and provides a smooth, silky, and luxurious feel to the composition.

In an exemplary embodiment, a cosmetic composition in the form of a stable, pleasant feeling W/O emulsion is provided. The composition includes an aqueous phase and an oil phase. The aqueous phase includes a water-soluble anti-aging active ingredient at a concentration, by weight, of about 0.5% to about 10%, based upon weight of the composition, and water. The oil phase includes an emulsifying crosslinked siloxane elastomer, at least one wax having a melting point greater than about 50° C., and an oil-soluble anti-aging active ingredient at a concentration, by weight, of about 0.1% to about 1%, based upon weight of the composition, oil, and optionally a branched- and/or linear-type silicone emulsifier. The cosmetic composition provides a velvety soft, melting and caring sensation upon application to the skin.

In another exemplary embodiment, a method for preparing the cosmetic composition is provided involving mixing the above-disclosed ingredients to form the composition.

The present disclosure is also directed to a method for cosmetic treatment of keratinous tissues by applying the above-disclosed composition onto a surface of the keratinous tissue.

Other features and advantages of the present invention will be apparent from the following more detailed description of the preferred embodiment which illustrates, by way of example, the principles of the invention.

DETAILED DESCRIPTION OF THE INVENTION

All numbers expressing quantities of ingredients and/or reaction conditions are to be understood as being modified in all instances by the term about, unless otherwise indicated.

"Keratinous tissue," as used herein, includes but is not limited to skin, hair, and nails.

In the present application the term "ambient temperature" means a temperature of about 25° C.

The cosmetic compositions and methods of the present invention can comprise, consist of, or consist essentially of the essential elements and limitations of the invention described herein, as well as any additional or optional ingredients, components, or limitations described herein or otherwise useful in personal care compositions intended for topical application to keratinous tissue.

Applicants have surprisingly discovered a W/O emulsion which can incorporate high levels of skin care active ingredients which are normally difficult to formulate in cosmetic compositions. The resulting W/O emulsion has a velvety soft, melting and caring sensation when applied to the skin and does not suffer from the usual undesirable attributes of W/O emulsions such as tackiness, greasiness, and or poor spreadability.

One advantage of an embodiment of the present disclosure includes providing a cosmetic composition for incorporating relatively high levels of skin care active ingredients that are normally difficult to formulate in cosmetic compositions. Another advantage of an embodiment of the present disclosure includes providing cosmetic compositions that provide improved skin-feel properties.

The W/O emulsion of the present cosmetic composition has a white, glossy cream appearance. When the cosmetic composition is applied onto the skin in a conventional way, the cosmetic composition has a velvety soft, melting and caring sensation, and is not tacky.

Aqueous Phase

The aqueous phase present in the cosmetic composition according to the disclosure includes water, a water-soluble anti-aging active ingredient, and other aqueous phase ingredients. The aqueous phase of the W/O emulsion cosmetic composition is at a concentration, by weight, of about 50% to about 90%, or alternatively about 60% to about 90%, or alternatively about 70% to about 90%, based upon weight of the cosmetic composition.

Water-Soluble Anti-Aging Active Ingredient

The aqueous phase present in the cosmetic composition according to the disclosure includes a water-soluble anti-aging active ingredient, by weight, of about 0.5% to about 10%, or alternatively about 0.5% to about 5%, or alternatively about 1% to about 3%, based upon weight of the composition.

Suitable examples of water-soluble anti-aging active ingredient include, for example, C-glycoside derivatives. C-glycoside derivatives may provide the composition of the invention with anti-ageing care properties, in particular by exerting an effect of hydration of the skin and by filling wrinkles over a period of time.

A C-glycoside derivative of the invention may have the following general formula (I):

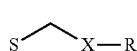

(I)

in which:

R represents a linear, saturated $C_1$-$C_{20}$ alkyl, perfluoroalkyl or hydrofluoroalkyl radical, in particular, $C_2$-$C_{10}$, or unsaturated $C_2$-$C_{20}$, in particular, $C_3$-$C_{10}$, branched or cyclic, saturated or unsaturated, $C_3$-$C_{20}$, in particular, $C_4$-$C_{10}$, a phenyl or benzyl radical:

said radical optionally being interrupted by one or more heteroatoms selected from oxygen, sulfur, nitrogen, and silicon; and optionally being substituted with at least one radical selected from —$OR_1$, —$SR_1$, —$NR_1R_2$, —$COOR_1$, —$CONHR_1$, —CN, a halogen atom, a $C_1$-$C_6$ perfluoroalkyl or hydrofluoroalkyl radical, a $C_3$-$C_8$ cycloalkyl or heterocyclic radical or a $C_6$-$C_{10}$ aryl radical, optionally substituted;

where $R_1$ and $R_2$ may be identical or different, representing a hydrogen atom, a hydroxy radical, a linear, saturated, $C_1$-$C_{30}$ alkyl, perfluoroalkyl or hydrofluoroalkyl radical, in particular, $C_2$-$C_{12}$, or unsaturated $C_2$-$C_{30}$, in particular $C_3$-$C_{12}$ or branched or cyclic, saturated or unsaturated $C_3$-$C_{30}$, in particular $C_4$-$C_{12}$, or a $C_6$-$C_{10}$ aryl radical;

X represents a radical selected from: —C(O)—, —CH($NR_3R_4$)—, —$CHR_5$—, —C(=$CHR_5$)—, with $R_3$, $R_4$ and $R_5$, which may be identical or different, representing a hydrogen atom, a hydroxy radical or a radical R, as defined above;

mS represents a monosaccharide or a polysaccharide with up to 20 units of sugar, in the pyranose and/or furanose form, and of the L and/or D series;

the S—$CH_2$—X linkage represents a C-anomeric type linkage, especially of type α or β, and more particularly type β; and physiologically acceptable salts thereof, and its optical and/or geometric isomers, alone or as a mixture.

The optical and/or geometric isomers, as well as physiologically acceptable salts, of the C-glycoside derivatives with formula (I) may be used alone or as a mixture in any proportion.

A C-glycoside derivative of the invention may in particular be obtained by the synthesis method described in the document WO 02/051828.

The C-glycoside derivative salts of the invention may comprise conventional physiologically acceptable salts of these compounds, such as those formed from organic or inorganic acids.

Examples of salts of mineral acids that may be mentioned are sulfuric acid, hydrochloric acid, hydrobromic acid, hydroiodic acid, phosphoric acid and boric acid. It is also possible to mention salts of organic acids that may comprise one or more carboxylic, sulfonic or phosphonic acid groups. They may be linear, branched or cyclic aliphatic acids, or aromatic acids. These acids may also comprise one or more heteroatoms selected from O and N, for example in the form of hydroxy groups. The following may in particular be mentioned: propionic acid, acetic acid, terephthalic acid, citric acid and tartric acid.

A particularly suitable water-soluble anti-aging active ingredient for use with the present invention is a C-glycoside derivative. A preferred C-glycoside derivative is hydroxypropyl tetrahydropyrantriol, also named C-β-D-xylopyranoside-2-hydroxy propane, sold under the trade name Mexoryl SBB® by Chimex.

In one embodiment, hydroxypropyl tetrahydropyrantriol is incorporated in the cosmetic composition at levels of about 0.5% to about 10%, or alternatively about 0.5% to about 5%, or alternatively about 1% to about 3%, based upon weight of the composition.

Water

The aqueous phase present in the cosmetic composition according to the disclosure includes water at a concentration, by weight, of about 40% to about 80%, or alternatively about 45% to about 75% or alternatively about 50% to about 60%, based upon weight of the composition. The water used may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

Oil Phase

The oil phase present in the cosmetic composition according to the disclosure includes an emulsifying crosslinked siloxane elastomer, at least one wax having a melting point greater than about 50° C., an oil-soluble anti-aging active ingredient, oil, and optionally a branched- and/or linear-type silicone emulsifier. The oil phase is at a concentration, by weight, of about 10% to about 40%, or alternatively about 10% to about 30%, or alternatively about 10% to about 25%, based upon weight of the cosmetic composition.

Emulsifying Crosslinked Siloxane Elastomer

The oil phase present in the cosmetic composition according to the disclosure includes an emulsifying crosslinked siloxane elastomer at a concentration, by weight, of about 0.1% to about 20%, or alternatively about 0.5% to about 10%, or alternatively about 1% to about 5%, based upon weight of the composition.

Examples of suitable emulsifying crosslinked siloxane elastomers, include, but are not limited to, substituted or unsubstituted dimethicone/copolyol crosspolymer, dimethicone/PEG-10/15 crosspolymers, substituted or unsubstituted dimethicone/polyglyceryl crosspolymer, dimethicone/polyglycerin-3 crosspolymer. Such suitable emulsifying crosslinked siloxane elastomers are sold or made, for example, under the names of "KSG-210" a polyether-modified cross polymer with an INCI name of dimethicone (and) dimethicone/PEG-10/15 crosspolymer, and "KSG-710" a polyglycerin-modified crosspolymer with an INCI name of dimethicone (and) dimethicone/polyglycerin-3 crosspolymer, both available from Shin-Etsu Silicones of America, Inc. (Akron, Ohio).

A particularly suitable emulsifying crosslinked siloxane elastomer for use with the present invention is dimethicone/PEG-10/15 crosspolymer (INCI name), sold under the trade name "KSG-210" by Shin-Etsu Silicones of America, Inc. (Akron, Ohio).

In one embodiment, dimethicone/PEG-10/15 crosspolymer is incorporated in the cosmetic composition at levels of about 0.1% to about 20%, or alternatively about 0.5% to about 10%, or alternatively about 1% to about 5%, based upon weight of the composition.

Oil-Soluble Anti-Aging Active Ingredient

The oil phase present in the cosmetic composition according to the disclosure includes an oil-soluble anti-aging active ingredient, by weight, of about 0.1% to about 1%, or alternatively about 0.1% to about 0.5%, or alternatively about 0.1% to about 0.3%, based upon weight of the composition.

Suitable examples of oil-soluble anti-aging active ingredient include, for example, salicylic acid derivatives. Salicylic acid derivatives may provide the composition of the invention with anti-ageing care properties, in particular by effecting desquamation of the skin and/or for stimulating epidermal renewal and promoting skin exfoliation thereby improving radiance of the complexion, improving skin texture, smoothing the skin's microrelief, reducing pore size, or reducing skin discolorations over a period of time.

The lipophilic salicylic acid derivatives in accordance with the invention correspond to the formula (II)

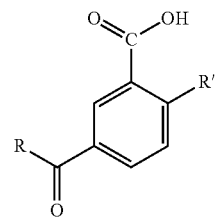

(II)

in which:

the R radical denotes a linear, branched or cyclic, saturated aliphatic chain containing from 2 to 22 carbon atoms; an unsaturated chain containing from 2 to 22 carbon atoms and comprising one or more double bonds that may be conjugated; an aromatic ring bonded to the carbonyl radical directly or via saturated or unsaturated aliphatic chains containing from 2 to 7 carbon atoms; it being possible for said rings and chains to be substituted with one or more substituents, which may be identical or different, chosen from (a) halogen atoms, (b) a trifluoromethyl group, (c) hydroxyl groups in free form or esterified with an acid containing from 1 to 6 carbon atoms, or (d) a carboxyl function in free form or esterified with a lower alcohol containing from 1 to 6 carbon atoms;

R' is a hydroxyl group or an ester group of formula:

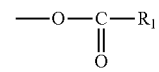

in which R1 denotes a linear or branched, saturated or unsaturated aliphatic chain containing from 1 to 18 carbon atoms;

and also salts thereof derived from an inorganic or organic base.

Preferentially, the R radical denotes a linear, branched or cyclic, saturated aliphatic chain containing from 3 to 11 carbon atoms; an unsaturated chain containing from 3 to 17 carbon atoms and comprising one or more conjugated or unconjugated double bonds; it being possible for said hydrocarbon-based chains to be substituted with one or more substituents, which may be identical or different, chosen from (a) halogen atoms, (b) a trifluoromethyl group, (c) hydroxyl groups in free form or esterified with an acid containing from 1 to 6 carbon atoms, or (d) a carboxyl function in free form or esterified with a lower alcohol containing from 1 to 6 carbon atoms;

R' is a hydroxyl group or an ester group of formula:

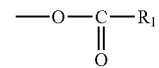

in which R1 denotes a radical —$(CH_2)_n$—$CH_3$ where n is a number ranging from 0 to 14;

and also salts thereof obtained by salification with an inorganic or organic base.

The compounds that are more particularly preferred are those in which the R radical is a C3-C11 alkyl group and R' denotes hydroxyl.

Other particularly advantageous compounds are those in which R represents a chain derived from linoleic, linolenic or oleic acid.

Another group of particularly preferred compounds is constituted of compounds in which the R radical denotes a C3-C11 alkyl group bearing a carboxyl function in free form or esterified with a lower alcohol containing from 1 to 6 carbon atoms and R' denotes hydroxyl. Lipophilic salicylic acid derivatives of formula (II) that may be used according to the invention are in particular described in U.S. Pat. No. 6,159,479 and U.S. Pat. No. 5,558,871, FR 2,581,542, U.S. Pat. No. 4,767,750, EP 378 936, U.S. Pat. No. 5,262,407, U.S. Pat. No. 5,667,789, U.S. Pat. No. 5,580,549 and EP-A-570,230.

Among the particularly suitable compounds of formula (II), mention may be made of 5-n-octanoylsalicylic acid (or capryloyl salicylic acid); 5-n-decanoylsalicylic acid; 5-n-dodecanoylsalicylic acid; 5-n-heptyloxysalicylic acid, and the corresponding salts thereof.

For the purposes of the invention, the salts of these acids are also considered.

The salts can be obtained by salification of the acid under consideration with an organic or inorganic base. By way of inorganic base, mention may particularly be made of alkali metal or alkaline-earth metal hydroxylated bases, for instance sodium hydroxide or potassium hydroxide, and ammonia.

As regards the organic bases, they may in particular be bases of amine or alkanolamine type.

A particularly suitable oil-soluble anti-aging active ingredient for use with the present invention is a salicylic acid derivative, preferably, capryloyl salicylic acid, also named 5-n-octanoylsalicylic acid, sold under the trade name Mexoryl SAB® by Chimex.

In one embodiment, capryloyl salicylic acid is incorporated in the cosmetic composition at levels of about 0.1% to about 1%, or alternatively about 0.1% to about 0.5%, or alternatively about 0.1% to about 0.3%, based upon weight of the composition.

By way of illustration, a particularly suitable combination of water-soluble anti-aging active ingredient and oil-soluble anti-aging active ingredient according to the invention is about 1% to about 3% by weight based upon the weight of the composition of hydroxypropyl tetrahydropyrantriol and about 0.1% to about 0.3% by weight based upon the weight of the composition of capryloyl salicylic acid.

Branched- and/or Linear-Type Silicone Emulsifier (Optional)

The oil phase present in the cosmetic composition according to the disclosure optionally may include a branched- and/or linear-type silicone emulsifier at a concentration, by weight, of about 0.1% to about 10%, or alternatively about 0.5% to about 5%, or alternatively about 1% to about 3%, based upon weight of the composition.

Suitable examples of branched- and/or linear-type silicone emulsifiers include, PEG-9 polydimethylsiloxyethyl dimethicone available under the tradename KF-6028 and PEG-9, lauryl PEG-9 polydimethylsiloxyethyl dimethicone available under the tradename KF-6038, both available from Shin-Etsu.

By way of illustration, a particularly suitable embodiment comprises a combination of emulsifying crosslinked siloxane elastomer and branched- and/or linear-type silicone emulsifier.

Wax

The oil phase present in the cosmetic composition according to the disclosure includes at least one wax having a melting point of greater than about 50° C., or alternatively greater than about 55° C., or alternatively greater than about 60° C. by weight, of about 1% to about 10%, or alternatively about 2% to about 8%, or alternatively about 4% to about 6%, based upon weight of the composition.

Suitable examples of wax(es) having a melting point of greater than about 50° C. include, for example hydrocarbon-based wax(es), fluoro wax(es) and/or silicone wax(es) and can be of vegetable, mineral, animal and/or synthetic origin.

Suitable wax(es) according to the present disclosure, include, but are not limited to, carnauba wax, candelilla wax, hydrogenated jojoba oil, rice bran wax, sunflower seed wax, vegetable wax, hydrogenated castor oil, waxes obtained by hydrogenation of olive oil esterified with fatty alcohols comprising a C12 to C18 chain sold by the company Sophim in the Phytowax® Olive range (16L55 and 18L57), waxes obtained by hydrogenation of castor oil esterified with fatty alcohols comprising a C12 to C18 chain sold by the company Sophim in the Phytowax® Castor range (16L64, 18L69, and 22L73), hydroxyoctacosanyl hydroxystearate, hydrogenated castor wax, rice bran wax, C20-40 alkyl stearate, alcohol polyethylene wax, microcrystalline wax, polyethylene wax, octanedioate, Fischer-Tropsch wax, Chinese insect wax, shellac wax, benehyl fumarate, and synthetic wax.

Particularly suitable waxes having a melting point greater than about 50° C. for use with the present invention are hydrogenated jojoba wax sold under the trade name "Jojoba Wax Flakes" by Desert Whale and synthetic wax sold under the tradename "Cirebelle 303" by Cirebelle.

In one embodiment, wax is incorporated in the cosmetic composition at levels of about 1% to about 10%, or alternatively about 2% to about 8%, or alternatively about 4% to about 6%, based upon weight of the composition.

By way of illustration, a particularly suitable combination of waxes according to the invention, is about 1% to about 4% by weight based upon the weight of the composition of hydrogenated jojoba oil and about 2% to about 6% by weight based upon the weight of the composition of synthetic wax.

Oil

The oil phase of the present disclosure contains a cosmetically acceptable oil or a mixtures thereof.

The oil may be selected from the group consisting of oils of animal or plant origin, mineral oils, synthetic glycerides, fatty esters, fatty alcohols, silicone oils, and aliphatic hydrocarbons. These materials may be volatile or non-volatile. Suitable examples of oils may be selected from aliphatic hydrocarbons, plant oils, fatty alcohols, esters of fatty alcohols and/or fatty acids other than animal or plant oils and synthetic glycerides, or mixtures thereof. Particularly suitable oils may be selected from the group consisting of plant oils, silicone oils, esters of fatty alcohols, and mixtures thereof.

As examples of plant oils, mention may be made of, for example, orbignya oleifera seed oil, linseed oil, camellia oil, macadamia nut oil, sunflower oil, apricot oil, soybean oil, arara oil, hazelnut oil, corn oil, mink oil, olive oil, avocado oil, sasanqua oil, castor oil, safflower oil, jojoba oil, sunflower oil, almond oil, grapeseed oil, sesame oil, soybean oil, peanut oil, and mixtures thereof. As examples of animal oils, mention may be made of, for example, squalene, perhydrosqualene, squalane, and mixtures thereof.

As examples of silicone oils, mention may be made of, for example, linear organopolysiloxanes such as dimethylpolysiloxane, methylphenylpolysiloxane, methylhydrogenpolysiloxane, and the like; cyclic organopolysiloxanes such as octamethylcyclotetrasiloxane, decamethylcyclopentasiloxane, dodecamethylcyclohexasiloxane, and mixtures thereof.

As examples of fatty esters, mention may be made of, for example, diisopropyl sebacate, ethyl laurate, butyl laurate, hexyl laurate, isohexyl laurate, isopropyl laurate, methyl myristate, ethyl myristate, butyl myristate, isobutyl myristate, isopropyl myristate, 2-octyldodecyl myristate, 2-ethylhexyl monococoate (or octyl monococoate), ethyl palmitate, isopropyl palmitate, isobutyl palmitate, 2-ethylhexyl palmitate (or octyl palmitate), butyl stearate, isopropyl stearate, isobutyl stearate, isocetyl stearate, isostearyl isostearate, isopropyl isostearate, 2-ethylhexyl stearate (or octyl stearate), 2-ethylhexyl hydroxystearate (or octyl hydroxystearate), decyl oleate, isononyl isononanoate, tridecyl neopentanoate, isocetyl neopentanoate, isostearyl neopentanoate, octyldodecyl neopentanoate and isoarachidyl neopentanoate, and mixtures thereof.

In one embodiment, oil is incorporated in the cosmetic composition at levels of about 5% to about 35%, or alternatively about 8% to about 30%, or alternatively about 10% to about 20%, based upon weight of the composition.

By way of illustration, a particularly suitable combination of oils according to the invention, is about 1% to about 5% by weight based upon the weight of the composition of orbignya olifera seed oil, about 1% to about 5% by weight based upon the weight of the composition of diisopropyl sebacate, and about 1% to about 20% by weight based upon the weight of the composition of dimethicone.

Optional Additives

The cosmetic composition of the present disclosure may optionally include cosmetic powders. The optional cosmetic powders provide formulas that are smoother and softer on the skin. Representative cosmetic powders include, but are not limited to talc, mica, magnesium carbonate, calcium carbonate, magnesium silicate, aluminum magnesium silicate, silica, titanium dioxide, zinc oxide, red iron oxide, yellow iron oxide, black iron oxide, polyethylene powder, methacrylate powder, polystyrene powder, silk powder, crystalline cellulose, starch, titanated mica, iron oxide titanated mica, bismuth oxychloride, and the like. Additional powders include, but are not limited to, inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide. A representative cosmetic powder includes, for example, polymethylsilsesquioxane. Cosmetic powders may be present in the compositions in amounts generally ranging from about 1% to about 15% by weight of the composition.

The cosmetic composition of the present disclosure may also contain cosmetically acceptable additives or adjuvants as well as cosmetic or dermatologic active agents. Representative additives and adjuvants include, for example, water-soluble or water-miscible solvents or co-solvents, dispersion enhancing agents, moisturizers, colorants, fillers, antioxidants (e.g., EDTA, BHT, tocopherol), essential oils, fragrances, dyes, neutralizing or pH-adjusting agents (e.g., citric acid, triethylamine (TEA) and sodium hydroxide), conditioning or softening agents (e.g., panthenol and allantoin) and extracts such as botanical extracts. Additives and adjuvants may be present in the compositions in amounts generally ranging from about 0.01% to about 10% by weight. Examples of cosmetic active agents or dermatological active agents include sunscreen agents (e.g., inorganic sunscreen agent, such as titanium dioxide and zinc oxide and organic sunscreen agents, such as octocrylene, ethylhexyl salicylate, homosalate, and avobenzone), free-radical scavengers, vitamins (e.g., Vitamin E and derivatives thereof), anti-elastase and anti-collagenase agents, peptides, fatty acid derivatives, steroids, trace elements, extracts of algae and of planktons, enzymes and coenzymes, flavonoids and ceramides, hydroxy acids and mixtures thereof, and enhancing agents. These ingredients may be soluble or dispersible in any water phase(s) or oil phase(s) that is/are present in the cosmetic composition (i.e., aqueous and/or fatty (oil) phase).

Accelerated Stability Studies

As a means to determine the shelf life of a cosmetic composition and to predict its real time stability, accelerated stability studies were carried out simulating possible storage conditions such as various storage temperatures (5° C., 25° C., 37° C. and 45° C., for example) for a period of 8 weeks and freeze-thaw cycles (−20° C. to 25° C. cycles with each temperature set for 12 hours). In this invention, the storage stability study at 25° C. and 45° C. provides the most relevant and discerning results concerning the formula stability. Thus the viscosity measurements were used as the primary criteria for composition storage stability, in addition to the visual assessment for any signs of loss of homogeneity and/or phase separation.

Viscosity

Viscosity was measured at 25° C. using a Rheomat RM180 Viscometer with concentric measuring systems, where a properly-chosen spindle was allowed to rotate within the test formula and a single point measurement was taken after 10 minutes with shear rate at 200 $s^{-1}$. Those skilled in the art may select the spindle for measuring the viscosity from spindles M3 or M4 on the basis of their general knowledge, so as to be able to perform the measurement. Viscosity is measured in UD (units of deviation).

Viscosity measurements were taken initially and after 8 weeks storage at selected temperatures. Samples were classified as stable if the viscosity did not change by more than about one-third of the initial value over the 8-week period. Samples were classified as unstable if the viscosity changed by more than about one-third of the initial value after the 8-week period, and/or the formulas exhibited signs of loss of homogeneity and/or phase separation.

The following examples are intended to further illustrate the present invention. They are not intended to limit the invention in any way. Unless otherwise indicated, all parts are by weight.

EXAMPLES

TABLE 1

Inventive Examples

| Phase | INCI US Name | Example 1 | Example 2 |
|---|---|---|---|
| A | DIMETHICONE (and) DIMETHICONE/PEG-10/15 CROSSPOLYMER (KSG-210 from Shin Etsu) | 5 | 5 |
| A | PEG-9 POLYDIMETHYLSILOXYETHYL DIMETHICONE (and) PEG-9 (KF 6028 from Shin Etsu) | 1 | 0 |
| A | LAURYL PEG-9 POLYDIMETHYL-SILOXYETHYL DIMETHICONE (KF 6038 from Shin Etsu) | 0 | 1 |
| A | DIMETHICONE | 4 | 4 |
| A | ORBIGNYA OLEIFERA SEED OIL | 2 | 2 |
| A | DIISOPROPYL SEBACATE | 2 | 2 |
| A | OCTYLDODECANOL | 3 | 3 |
| A | CAPRYLOYL SALICYLIC ACID | 0.3 | 0.3 |
| A | PRESERVATIVE | 0.15 | 0.15 |
| A | ACRYLATES/STEARYL ACRYLATE/DIMETHICONE METHACRYLATE COPOLYMER | 1 | 1 |
| B1 | WATER | 53.55 | 53.55 |
| B1 | HYDROXYETHYLCELLULOSE | 0.2 | 0.2 |
| B1 | SODIUM HYALURONATE | 0.1 | 0.1 |
| B2 | GLYCERIN | 7 | 7 |
| B2 | ADENOSINE | 0.1 | 0.1 |
| B2 | DISODIUM EDTA | 0.1 | 0.1 |
| B2 | PRESERVATIVE | 0.5 | 0.5 |
| C | HYDROGENATED JOJOBA OIL | 2 | 2 |
| C | SYNTHETIC WAX | 4 | 4 |
| D | WATER | 4 | 4 |
| D | PROPYLENE GLYCOL | 3 | 3 |
| D | HYDROXYPROPYL TETRAHYDRO-PYRANTRIOL | 3 | 3 |
| E | POWDERS | 4.7 | 4.7 |
| F | FRAGRANCE | 0.3 | 0.3 |
| | Total (%): | 100 | 100 |
| | Initial Viscosity (Mobile 4, 10 min) UD | 29.3 | 24.1 |
| | 8 Week at 25° C. Viscosity (Mobile 4, 10 min) UD | 25.4 | 22.0 |
| | 8 Week at 45° C. Viscosity (Mobile 4, 10 min) UD | 20.2 | 17.2 |

TABLE 2

Comparative Examples

| Phase | INCI US Name | Example 3 | Example 4 |
|---|---|---|---|
| A | DIMETHICONE (and) DIMETHICONE/PEG-10/15 CROSSPOLYMER (KSG-210 from Shin Etsu) | 5 | 5 |
| A | PEG-10 DIMETHICONE | 0.1 | 0.1 |
| A | DIMETHICONE (and) DIMETHICONOL | 1 | 1 |
| A | DIMETHICONE | 10 | 10 |
| B | WATER | 59.05 | 58.55 |
| B | GLYCERIN | 15 | 15 |
| B | PROPANEDIOL | 5 | 5 |
| B | PRESERVATIVES | 0.15 | 0.15 |
| B | DISODIUM EDTA | 0.1 | 0.1 |
| B | SODIUM CITRATE | 0.2 | 0.2 |
| B | SODIUM CHLORIDE | 0.8 | 0.8 |
| C | ALCOHOL DENAT. | 3 | 3 |
| C | CAPRYLOYL SALICYLIC ACID | 0.1 | 0.1 |
| C | PRESERVATIVES | 0.5 | 0.5 |
| D | POWDERS | 0 | 0.5 |
| | Total (%): | 100 | 100 |
| | Initial Viscosity (Mobile 4, 10 min): | 16.1 | 27.4 |
| | 8 Week at 25° C. Viscosity (Mobile 4, 10 min): | 8.1 | 19.4 |
| | 8 Week at 45° C. Viscosity (Mobile 4, 10 min): | too low to measure | phase separated |

The method of making each of the examples provided in Tables 1 and 2 are generally the same.

In making each of the examples in Tables 1 and 2, the following procedure is used.

The ingredients of Phase B1 (aqueous) were mixed together in a side beaker, and the contents were heated to 75° C. while mixing until a clear liquid was obtained. The ingredients of Phase B2 were added to the beaker while mixing. The ingredients of Phase A (oil phase) were added to the main kettle and heated to 85-90° C. while mixing until a homogenous paste was obtained. The contents of the beaker (Phases B1 and B2) were slowly added to the main kettle while mixing. The ingredients of Phase C were added to the main kettle while mixing at 85-90° C. until waxes were fully melted. Heating was discontinued, and contents of the main kettle were allowed to cool. The ingredients of Phase D were added to the main kettle while mixing. Once the contents of the kettle reached 60-65° C., the ingredients of Phase E were added to the main kettle while mixing. Once the contents of the kettle reached 50° C., the ingredients of Phase F were added to the main kettle while mixing.

The viscosity of the emulsion was measured after preparation. Samples of the emulsions were subjected to storage conditions of 25° C. and 45° C. for 8 weeks after which the viscosity was again measured. Differences between the initial viscosity measurements and 8-week measurements indicated that the emulsions according to the invention, Examples 1 and 2 were stable. Conversely, comparative examples, Examples 3 and 4 were not stable, which was indicated by a drop in viscosity of greater than about one-third of the initial value after 8 weeks or phase separation. Comparative Examples 3 and 4 demonstrate the instability of a classical W/O emulsion comprising capryloyl salicylic acid, an oil-soluble anti-aging active ingredient.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A composition comprising:
   (a) an aqueous phase containing:
      (i) from about 0.5% to about 10% by weight, of at least one water-soluble active ingredient comprising a C-glycoside derivative; and
      (ii) water; and
   (b) an oil phase containing:
      (iii) at least one emulsifying crosslinked siloxane elastomer;
      (iv) from about 0.1% to about 1% by weight, of at least one oil-soluble active ingredient;
      (v) from about 1% to about 10% by weight, of a combination of at least two waxes comprising a first wax and at least one second wax, at least one of the at least two waxes having a melting point greater than about 50° C., wherein the first wax includes hydrogenated jojoba oil and the at least one second wax is selected from the group consisting of hydrocarbon-based wax, fluoro wax, silicone wax, and mixtures thereof; and
      (vi) from about 1% to about 35% by weight, of at least one oil selected from the group consisting of diisopropyl sebacate, ethyl laurate, butyl laurate, hexyl laurate, isohexyl laurate, isopropyl laurate, methyl myristate, ethyl myristate, butyl myristate, isobutyl myristate, isopropyl myristate, 2-octyldodecyl myristate, 2-ethylhexyl monococoate, octyl monococoate, ethyl palmitate, isopropyl palmitate, isobutyl palmitate, butyl stearate, isopropyl stearate, isobutyl stearate, isocetyl stearate, isostearyl isostearate, isopropyl isostearate, 2-ethylhexyl stearate, octyl stearate, 2-ethylhexyl hydroxystearate, octyl hydroxystearate, decyl oleate, tridecyl neopentanoate, isocetyl neopentanoate, isostearyl neopentanoate, octyldodecyl neopentanoate and isoarachidyl neopentanoate, orbignya oleifera seed oil, linseed oil, camellia oil, macadamia nut oil, sunflower oil, apricot oil, soybean oil, arara oil, hazelnut oil, corn oil, mink oil, olive oil, avocado oil, sasanqua oil, castor oil, safflower oil, almond oil, grapeseed oil, sesame oil, soybean oil, peanut oil, squalene, perhydrosqualene, squalane, and mixtures thereof; and,
   (c) at least one cosmetic powder present in an amount of from about 1% to about 15% by weight;
   wherein the composition is a water-in-oil emulsion; all weights based on the total weight of the composition.

2. The composition of claim 1 wherein the C-glycoside derivative is hydroxypropyl tetrahydropyrantriol.

3. The composition of claim 2 wherein the at least one emulsifying crosslinked siloxane elastomer (iii) includes dimethicone/PEG-10/15 crosspolymer.

4. The composition of claim 3 wherein the at least one oil-soluble active ingredient (iv) includes capryloyl salicylic acid.

5. The composition of claim 4 wherein the at least one water-soluble active ingredient (i) is present in an amount of from about 0.5% to about 5% by weight, based on the total weight of the composition.

6. The composition of claim 5 wherein the at least one emulsifying crosslinked siloxane elastomer (iii) is present in an amount of from about 0.1% to about 20% by weight, based on the total weight of the composition.

7. The composition of claim 6 wherein at least one oil-soluble active ingredient (iv) is present in an amount of from about 0.1% to about 0.5% by weight, based on the total weight of the composition.

8. The composition of claim 1 further comprising a branched- and/or linear-type silicone emulsifier present in an amount of from about 0.1% to about 10% by weight, based upon the total weight of the composition.

9. The composition of claim 1 wherein the first wax is present in an amount of from about 1% to about 4% by weight, and the at least one second wax is present in an amount of from about 2% to about 6% by weight, each based on the total weight of the composition, and the at least one second wax includes one or more of a synthetic wax and an acrylates/stearyl acrylate/dimethicone methacrylate copolymer silicone wax.

10. The composition of claim 9, wherein the at least one second wax includes a synthetic wax.

11. The composition of claim 9 wherein the at least one oil (vi) is selected from orbignya oleifera seed oil, diisopropyl sebacate, and mixtures thereof.

12. The composition of claim 11 wherein the oil (vi) is present in amount from about 5% to about 35% by weight, based upon the weight of the composition.

13. The composition of claim 1, further comprising one or a combination of glycerin, propylene glycol, and sodium hyaluronate.

14. The composition of claim 1, further comprising an acrylates/stearyl acrylate/dimethicone methacrylate copolymer present in an amount of 1% by weight, based on the total weight of the composition.

15. The composition of claim 1, wherein the composition has a viscosity that does not change by more than one-third of the initial value over eight weeks at a temperature of 45° C.

16. A composition comprising:
   (a) an aqueous phase containing:
      (i) from about 1% to about 3% by weight, of at least one water-soluble active ingredient comprising hydroxypropyl tetrahydropyrantriol; and
      (ii) water; and
   (b) an oil phase containing:
      (iii) from about 1% to about 5% by weight of at least one emulsifying crosslinked siloxane elastomer comprising dimethicone/PEG-10/15 crosspolymer;
      (iv) from about 0.1% to about 0.3% by weight, of at least one oil-soluble active ingredient comprising capryloyl salicylic acid;
      (v) from about 1% to about 10% by weight of a combination of at least two waxes comprising a first wax and at least one second wax, wherein the first wax includes hydrogenated jojoba oil, and the at least one second wax is selected from the group consisting of hydrocarbon-based wax, fluoro wax, silicone wax, and mixtures thereof; and
      (vi) from about 1% to about 35% by weight, of at least one oil selected from the group consisting of diisopropyl sebacate, ethyl laurate, butyl laurate, hexyl laurate, isohexyl laurate, isopropyl laurate, methyl myristate, ethyl myristate, butyl myristate, isobutyl myristate, isopropyl myristate, 2-octyldodecyl myristate, 2-ethylhexyl monococoate, octyl monococoate, ethyl palmitate, isopropyl palmitate, isobutyl palmitate, butyl stearate, isopropyl stearate, isobutyl stearate, isocetyl stearate, isostearyl isostearate, isopropyl isostearate, 2-ethylhexyl stearate, octyl stearate, 2-ethylhexyl hydroxystearate, octyl hydroxystearate, decyl oleate, tridecyl neopentanoate, isocetyl neopentanoate, isostearyl neopentanoate, octyldodecyl neopentanoate and isoarachidyl neopentanoate, orbignya oleifera seed oil, linseed oil, camellia oil, macadamia nut oil, sunflower oil, apricot oil, soybean oil, arara oil, hazelnut oil, corn oil, mink oil, olive oil, avocado oil, sasanqua oil, castor oil, safflower oil, almond oil, grapeseed oil, sesame oil, soybean oil, peanut oil, squalene, perhydrosqualene, squalane, and mixtures thereof; and, (c) at least one cosmetic powder present in an amount of from about 1% to about 15% by weight;

wherein the composition is a water-in-oil emulsion; all weights based on the total weight of the composition.

17. The composition of claim 12, wherein:
the oil (vi) includes orbignya oleifera seed oil present in an amount of from about 1% to about 5% by weight, and diisopropyl sebacate present in an amount of from about 1% to about 5% by weight, and the composition further comprises dimethicone present in an amount of from about 1% to about 20% by weight, and at least one branched- and/or linear-type silicone emulsifier present in an amount of from about 0.1% to about 10% by weight, and an acrylates/stearyl acrylate/dimethicone methacrylate copolymer present in an amount of 1% by weight, based on the total weight of the composition, and
the cosmetic powder is present in an amount of 4.7% by weight, based on the total weight of the composition.

18. The composition of claim 16, wherein the oil (vi) includes orbignya oleifera seed oil or diisopropyl sebacate.

19. The composition of claim 18, wherein:
the oil (vi) includes orbignya oleifera seed oil present in an amount of from about 1% to about 5% by weight and diisopropyl sebacate present in an amount of from about 1% to about 5% by weight, and the composition further comprises dimethicone present in an amount of from about 1% to about 20% by weight, and at least one branched- and/or linear-type silicone emulsifier present in an amount of from about 0.1% to about 10% by weight, and an acrylates/stearyl acrylate/dimethicone methacrylate copolymer present in an amount of 1% by weight, based on the total weight of the composition, and
the cosmetic powder is present in an amount of 4.7% by weight, based on the total weight of the composition.

20. The composition of claim 16, wherein the at least one second wax includes a synthetic wax.

21. The composition of claim 16, wherein the composition has a viscosity that does not change by more than one-third of the initial value over eight weeks at a temperature of 45° C.

22. A method of making a composition comprising:
(a) providing an aqueous phase containing the components:
(i) from about 0.5% to about 10% by weight, of at least one water-soluble active ingredient comprising a C-glycoside derivative; and
(ii) water;
(b) providing an oil phase containing the components:
(iii) at least one emulsifying crosslinked siloxane elastomer;
(iv) from about 0.1% to 1% by weight, of at least one oil-soluble anti-aging active ingredient;
(v) from about 1% to about 10% by weight, of a combination of at least two waxes comprising a first wax and at least one second wax, at least one of the at least two waxes having a melting point greater than about 50° C., wherein the first wax includes hydrogenated jojoba oil and the at least one second wax is selected from the group consisting of hydrocarbon-based wax, fluoro wax, silicone wax, and mixtures thereof; and
(vi) oil; all weights based on the total weight of the composition;
(c) providing at least one cosmetic powder present in an amount of from about 1% to about 15% by weight; and
(d) contacting the components of phases (a) and (b) and (c) so as to form a water-in-oil emulsion.

23. The method of claim 22, wherein the composition has a viscosity that does not change by more than one-third of the initial value over eight weeks at a temperature of 45° C.

24. A method of enhancing the appearance of a keratinous substrate comprising:
contacting the substrate with a composition comprising:
(a) an aqueous phase containing:
(i) from about 1% to about 3% by weight, of at least one water-soluble active ingredient comprising hydroxypropyl tetrahydropyrantriol; and
(ii) water; and
(b) an oil phase containing:
(iii) from about 1% to about 5% by weight of at least one emulsifying crosslinked siloxane elastomer comprising dimethicone/PEG-10/15 crosspolymer;
(iv) from about 0.1% to about 0.3% by weight, of at least one oil-soluble active ingredient comprising capryloyl salicylic acid;
(v) from about 1% to about 10% by weight, of a combination of at least two waxes comprising a first wax and at least one second wax, at least one of the at least two waxes having a melting point greater than about 50° C., wherein the first wax includes hydrogenated jojoba oil and the at least one second wax is selected from the group consisting of hydrocarbon-based wax, fluoro wax, silicone wax, and mixtures thereof; and
(vi) from about 1% to about 35% by weight, of at least one oil selected from the group consisting of silicone oil, diisopropyl sebacate, ethyl laurate, butyl laurate, hexyl laurate, isohexyl laurate, isopropyl laurate, methyl myristate, ethyl myristate, butyl myristate, isobutyl myristate, isopropyl myristate, 2-octyldodecyl myristate, 2-ethylhexyl monococoate, octyl monococoate, ethyl palmitate, isopropyl palmitate, isobutyl palmitate, butyl stearate, isopropyl stearate, isobutyl stearate, isocetyl stearate, isostearyl isostearate, isopropyl isostearate, 2-ethylhexyl stearate, octyl stearate, 2-ethylhexyl hydroxystearate, octyl hydroxystearate, decyl oleate, tridecyl neopentanoate, isocetyl neopentanoate, isostearyl neopentanoate, octyldodecyl neopentanoate and isoarachidyl neopentanoate, orbignya oleifera seed oil, linseed oil, camellia oil, macadamia nut oil, sunflower oil, apricot oil, soybean oil, arara oil, hazelnut oil, corn oil, mink oil, olive oil, avocado oil, sasanqua oil, castor oil, safflower oil, almond oil, grapeseed oil, sesame oil, soybean oil, peanut oil, squalene, perhydrosqualene, squalane, and mixtures thereof; and,
(c) at least one cosmetic powder present in an amount of from about 1% to about 15% by weight;
wherein the composition is a water-in-oil emulsion; all weights based on the total weight of the composition.

25. The method of claim 24, wherein the composition has a viscosity that does not change by more than one-third of the initial value over eight weeks at a temperature of 45° C.

* * * * *